(12) United States Patent
Que et al.

(10) Patent No.: US 7,708,745 B2
(45) Date of Patent: *May 4, 2010

(54) VARIABLE COMPOSITE SHEATH WITH INTERRUPTED SECTIONS

(75) Inventors: Like Que, Santa Clara, CA (US); George Bourne, Southborough, MA (US); Juli Curtis, Wilmington, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1056 days.

This patent is subject to a terminal disclaimer.

(21) Appl. No.: 11/193,626

(22) Filed: Aug. 1, 2005

(65) Prior Publication Data

US 2005/0277949 A1 Dec. 15, 2005

Related U.S. Application Data

(63) Continuation of application No. 10/147,938, filed on May 17, 2002, now Pat. No. 6,939,353, which is a continuation of application No. 09/548,405, filed on Apr. 12, 2000, now Pat. No. 6,398,791, which is a continuation-in-part of application No. 09/478,609, filed on Dec. 30, 1999, now Pat. No. 6,325,807.

(60) Provisional application No. 60/138,950, filed on Jun. 11, 1999.

(51) Int. Cl.
*A61B 17/22* (2006.01)

(52) U.S. Cl. .................. 606/127; 604/264; 604/265

(58) Field of Classification Search ............... 606/127, 606/128, 106, 170, 171, 206, 200; 604/524, 604/525, 264, 523, 527, 532, 265; 600/431, 600/435, 585

See application file for complete search history.

(56) References Cited

U.S. PATENT DOCUMENTS

| | | | |
|---|---|---|---|
| 1,612,697 A | 12/1926 | Cecil | |
| 1,677,671 A | 7/1928 | Councill | |
| 3,964,468 A | 6/1976 | Schulz | |
| 4,590,938 A | 5/1986 | Segura et al. | |
| 4,657,024 A | 4/1987 | Coneys | |
| 4,662,404 A | 5/1987 | LaVeen et al. | |
| 4,676,228 A | 6/1987 | Krasner et al. | |

(Continued)

FOREIGN PATENT DOCUMENTS

DE 36 41 935 A1 6/1987

(Continued)

OTHER PUBLICATIONS

English translation of Official Action from Japanese Patent Office dated Jan. 8, 2009 in Japanese Patent Application 2001-502749 (5 pages).

(Continued)

*Primary Examiner*—Pedro Philogene
(74) *Attorney, Agent, or Firm*—Finnegan Henderson Farabow Garrett & Dunner, L.L.P.

(57) ABSTRACT

A medical device includes a handle, a sheath, and an object-engaging unit. The distal end portion of the sheath is strong enough to resist being deformed by the object-engaging unit, yet another portion of the sheath is flexible enough to bend sufficiently.

18 Claims, 15 Drawing Sheets

U.S. PATENT DOCUMENTS

| | | | |
|---|---|---|---|
| 4,682,599 A * | 7/1987 | Konomura | 606/127 |
| 4,691,705 A * | 9/1987 | Okada | 606/127 |
| 4,768,505 A | 9/1988 | Okada et al. | |
| 4,865,017 A | 9/1989 | Shinozuka | |
| 5,057,114 A | 10/1991 | Wittich et al. | |
| 5,250,054 A | 10/1993 | Li | |
| 5,254,107 A | 10/1993 | Soltesz | |
| 5,358,493 A | 10/1994 | Schweich et al. | |
| 5,569,218 A * | 10/1996 | Berg | 604/525 |
| 5,601,583 A | 2/1997 | Donahue et al. | |
| 5,618,293 A | 4/1997 | Sample et al. | |
| 5,620,415 A | 4/1997 | Lucey et al. | |
| 5,620,447 A | 4/1997 | Smith et al. | |
| 5,632,734 A | 5/1997 | Galel et al. | |
| 5,639,276 A | 6/1997 | Weinstock et al. | |
| 5,695,482 A | 12/1997 | Kaldany | |
| 5,759,173 A | 6/1998 | Preissman et al. | |
| 5,782,834 A | 7/1998 | Lucey et al. | |
| 5,800,409 A | 9/1998 | Bruce | |
| 5,807,354 A | 9/1998 | Kenda | |
| 5,836,925 A | 11/1998 | Soltesz | |
| 5,888,436 A | 3/1999 | Keith et al. | |
| 5,897,537 A | 4/1999 | Berg et al. | |
| 5,911,715 A * | 6/1999 | Berg et al. | 604/525 |
| 5,944,728 A | 8/1999 | Bates | |
| 5,971,975 A * | 10/1999 | Mills et al. | 604/527 |
| 6,036,682 A | 3/2000 | Lange et al. | |
| 6,059,769 A * | 5/2000 | Lunn et al. | 604/523 |
| 6,398,791 B1 * | 6/2002 | Que et al. | 606/127 |
| 6,464,683 B1 * | 10/2002 | Samuelson et al. | 604/524 |
| 6,858,024 B1 * | 2/2005 | Berg et al. | 604/525 |
| 6,939,353 B2 * | 9/2005 | Que et al. | 606/127 |

FOREIGN PATENT DOCUMENTS

| | | |
|---|---|---|
| DE | 3641935 A1 | 6/1987 |
| EP | 0 702 936 A2 | 3/1996 |
| JP | 2-3624 | 1/1990 |
| JP | 3-32376 | 5/1991 |
| JP | 5-2166 | 1/1993 |
| JP | 5-38342 | 2/1993 |
| JP | 10-509616 | 9/1998 |
| JP | 10-263088 | 10/1998 |
| WO | WO 96/15824 | 5/1996 |

OTHER PUBLICATIONS

English translation of Official Action from Japanese Patent Office dated Sep. 16, 2009 in Japanese Patent Application 2001-502749 (4 pages).

* cited by examiner

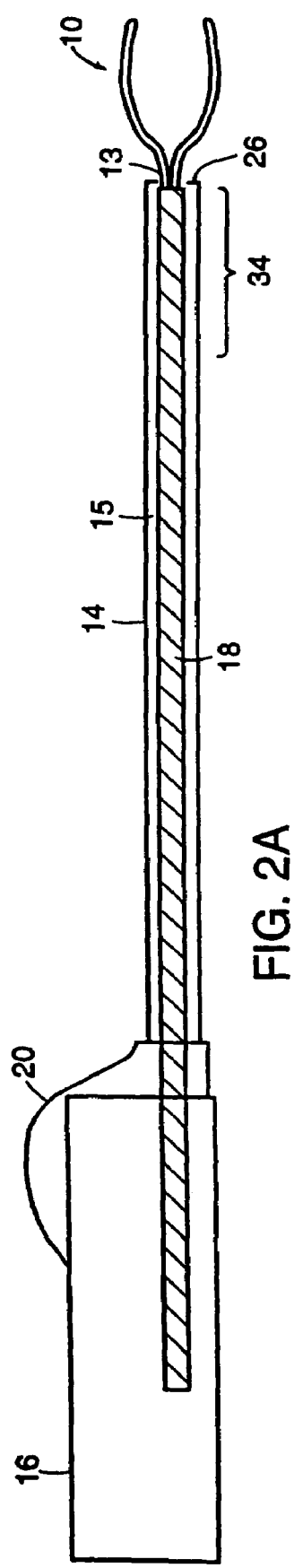
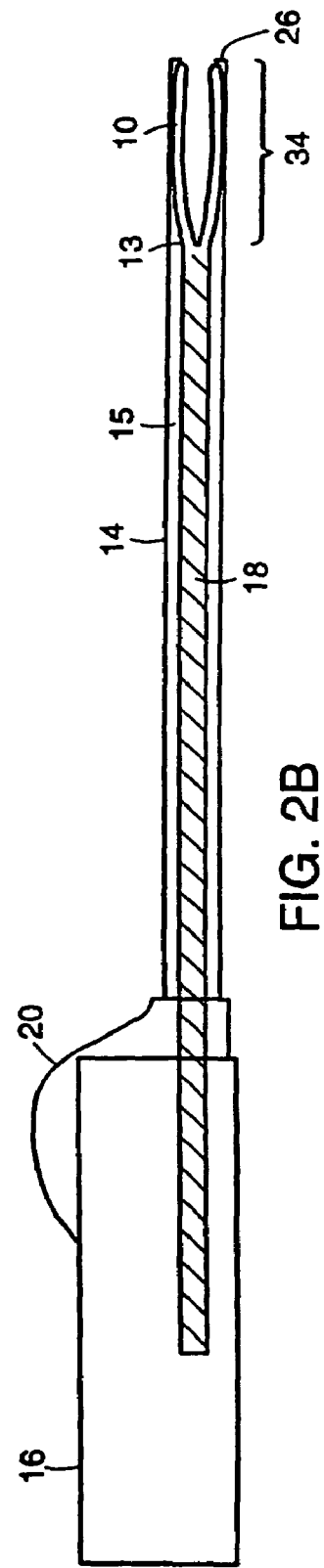
FIG. 2A
FIG. 2B

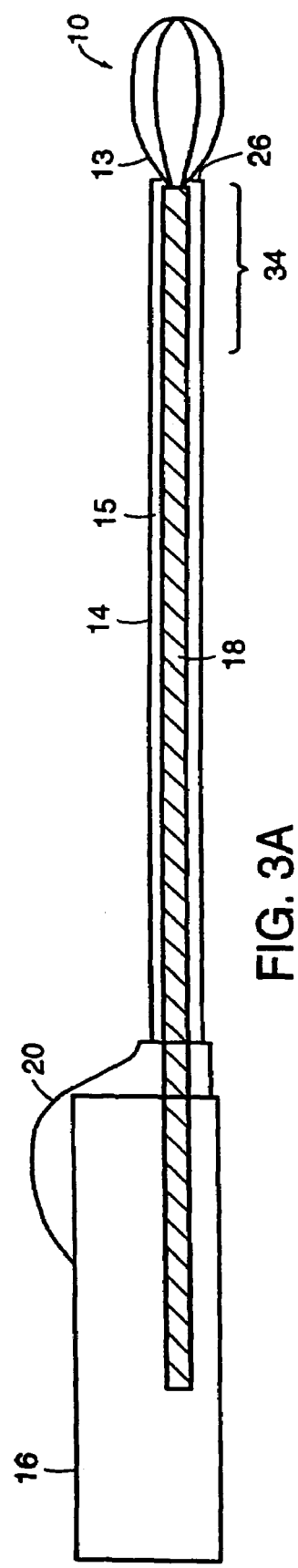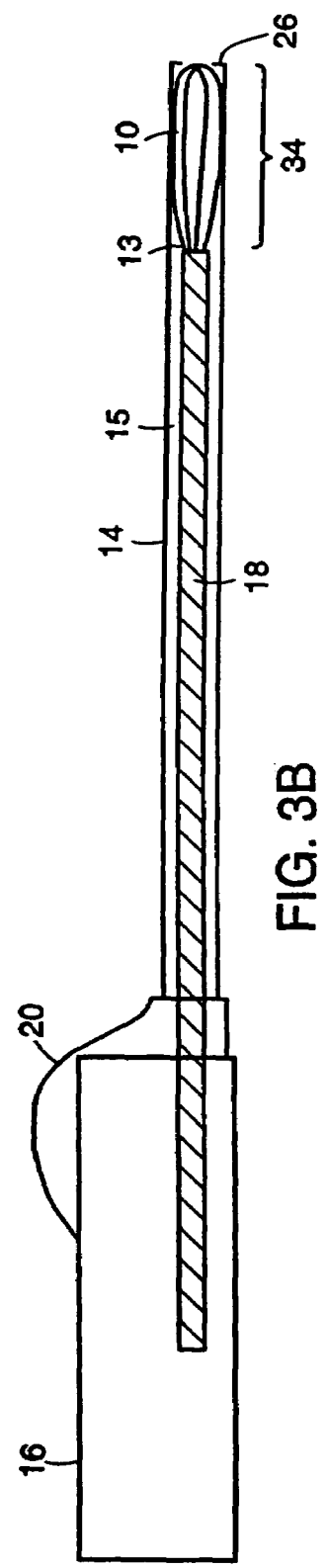
FIG. 3A
FIG. 3B

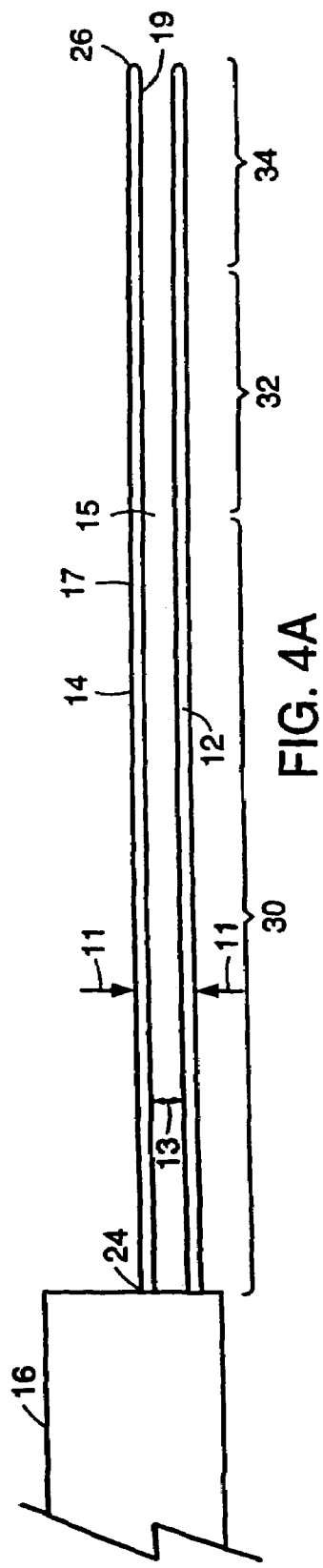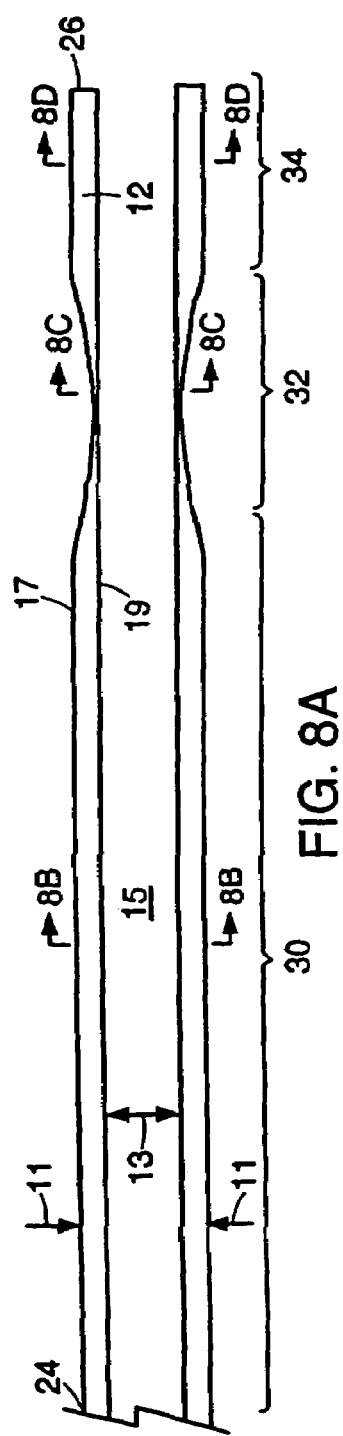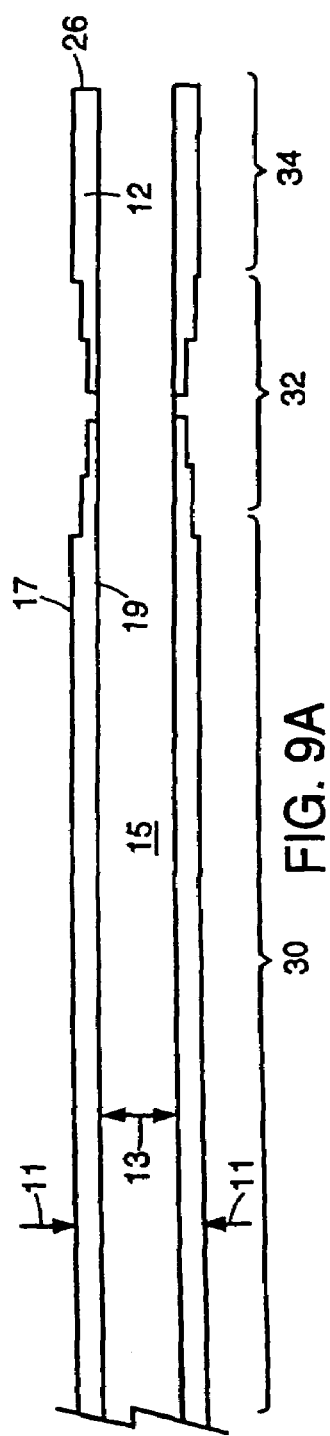

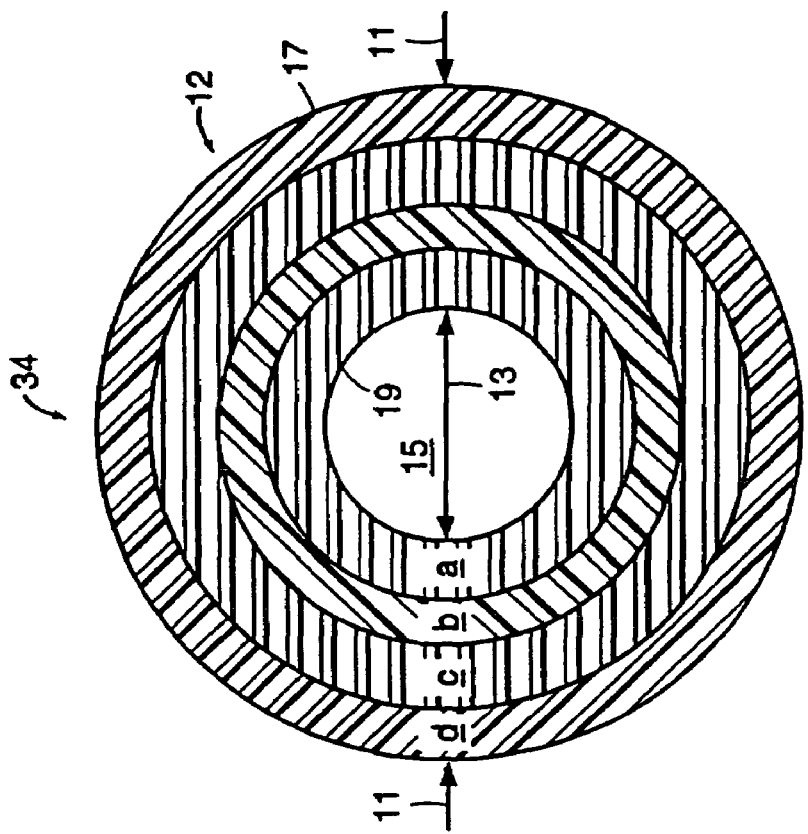
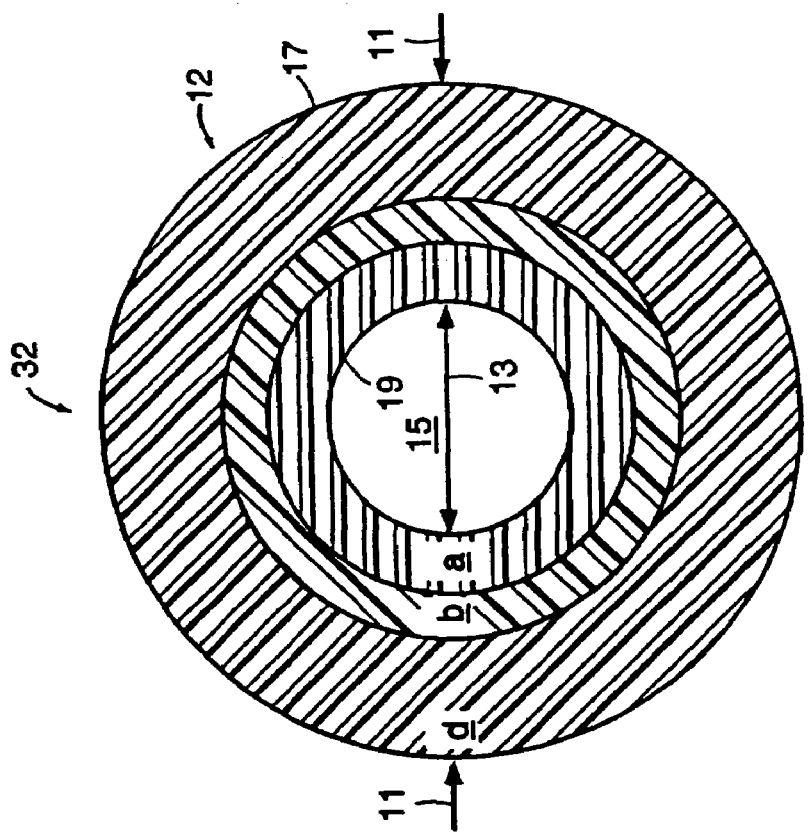

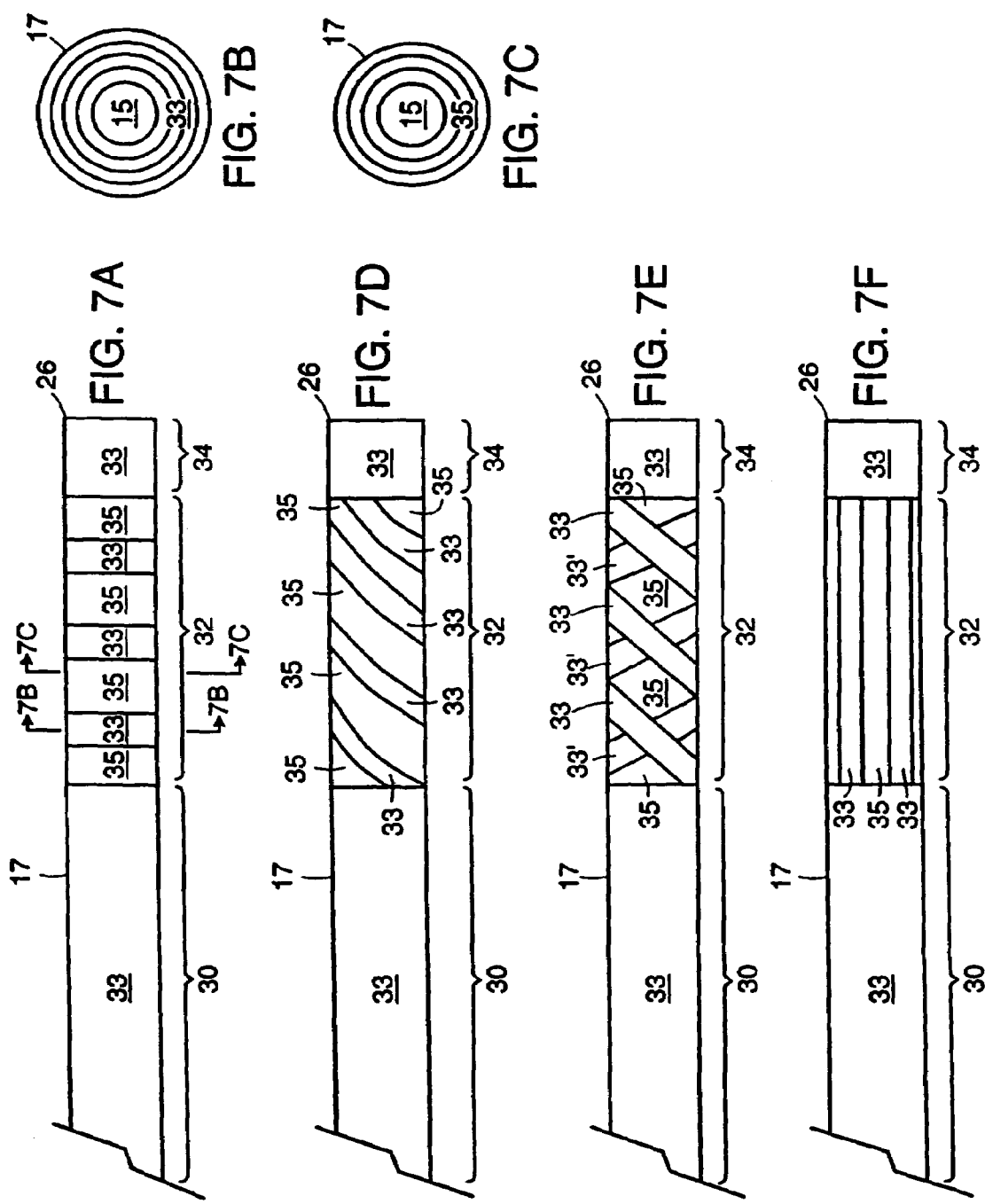

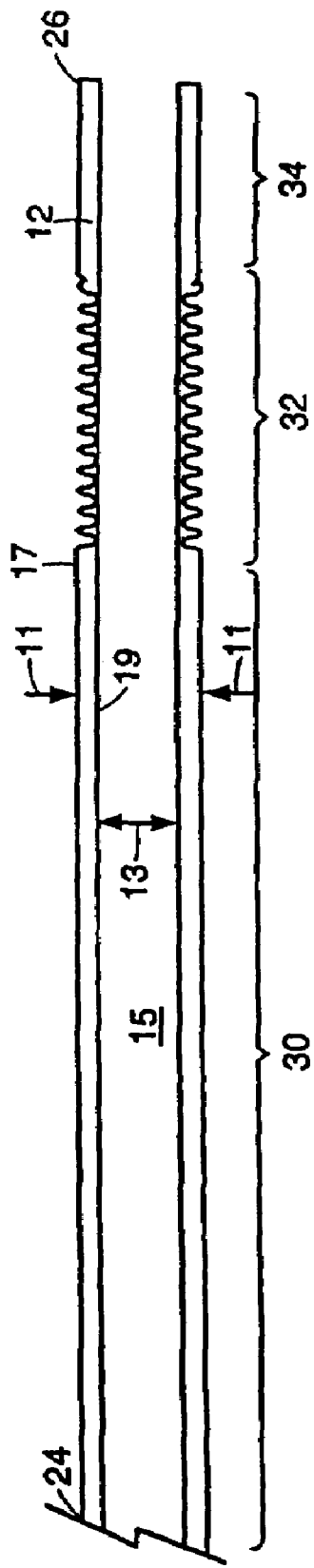
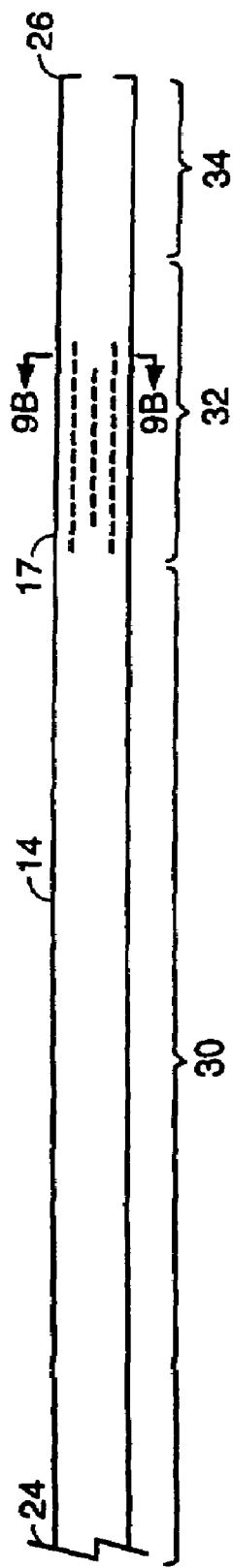

VARIABLE COMPOSITE SHEATH WITH INTERRUPTED SECTIONS

CROSS-REFERENCE TO RELATED APPLICATIONS

This is a continuation of U.S. patent application Ser. No. 10/147,938, filed May 17, 2002 now U.S. Pat. No. 6,939,353, which is a continuation of U.S. patent application Ser. No. 09/548,405, filed Apr. 12, 2000 (now U.S. Pat. No. 6,398, 791), which is a continuation-in-part of U.S. patent application Ser. No. 09/478,609, filed Dec. 30, 1999 (now U.S. Pat. No. 6,325,807), which claims the benefit of U.S. provisional application No. 60/138,950, filed Jun. 11, 1999, all of which are incorporated herein by reference.

TECHNICAL FIELD

This invention generally relates to medical devices for manipulating matter in a body. More particularly, the invention relates to a medical device including an object-engaging unit, such as a retrieval device or a surgical blade, and a sheath for introduction of the object-engaging unit directly into a body opening or cavity or into a body through an endoscope or a laparoscope channel, for example.

BACKGROUND INFORMATION

Medical devices can be used in a body opening, cavity, or tract to manipulate material within the body. Such medical devices may be used through an endoscope or a laparoscope. When inserted into a flexible endoscope, medical devices impair the ability of the flexible endoscope to achieve the desired flexion needed to engage material at a remote body site.

One such medical device has a sheath and an object-engaging unit, such as a basket, that is moveable relative to the sheath from a collapsed state within the sheath to another state in which the unit extends past the distal end of the sheath. Typically, the object-engaging unit is in an operational mode when the object-engaging unit is extended beyond the distal end of the sheath. The sheath typically extends from a handle, located at the proximal end (i.e., the end away from the patient) of the sheath, to the object-engaging unit, which is located at the distal end of the sheath (i.e., the end near the patient and that goes into the patient).

One purpose of the sheath is to collapse and release the object-engaging unit by sliding the sheath over (to collapse) or away from (to release) the object-engaging unit, or by moving the object-engaging unit into (to collapse) and out of (to release) the sheath. The object-engaging unit is, for example, a grasping forcep-like assembly, a basket assembly, or any type of tissue and/or object manipulating, capturing, and/or retrieving assembly. When the object-engaging unit is enclosed within the sheath, the object-engaging unit is inoperative and in its collapsed or withdrawn state. For example, object-engaging units, such as baskets, assume a collapsed, reduced diameter profile when the basket is enclosed within the distal end of the sheath. When the sheath is retracted relative to the basket or the basket is extended beyond the distal end of the sheath, the basket expands to a relatively larger diameter than when the basket is enclosed and collapsed within the sheath. In the expanded position, the basket is positioned and is operable at least to capture material in the body, such as kidney stones. If the object-engaging unit is, for example, a blade, it would be withdrawn when not needed to cut, and then extended at least partially out beyond the distal end of the sheath to allow cutting with the blade. The sheath also serves other purposes. For example, the sheath serves to encompass and protect the object-engaging unit as it is inserted into the body cavity or channel of an endoscope. The sheath also serves to protect the body cavity from damage that may be introduced by the object-engaging unit itself if it were released, expanded, or extended during passage of the sheath into the body. Also, the sheath must provide sufficient strength and rigidity to allow its insertion into the body or endoscope channel while also providing sufficient flexibility to permit the sheath to navigate through the tortuous channels of the body cavity, opening, or tract.

SUMMARY OF THE INVENTION

It is an object of the invention to provide a medical device comprising a sheath with sufficient flexibility to locate and engage material at a site in a body, such as the renal pelvis. That is, the sheath is sufficiently flexible to navigate the turns and curves of the body tract into which the medical device is introduced in order to manipulate target material at the remote body site. The sheath is also sufficiently flexible to allow a flexible endoscope, into which the sheath is inserted, to achieve the desired flexion.

It is another object of the invention to provide a medical device including a sheath that has sufficient strength at the proximal and distal end portions of the sheath to locate, engage, and retrieve target material at a remote body site, and to actuate an object-engaging unit without distorting or deforming the distal end portion of the sheath.

It is yet another object of the invention to provide a method of using medical devices including such sheaths to retrieve material at a remote site in a body.

In one aspect, the invention relates to a device for use in manipulating material at a site within a body. The device includes a handle and a sheath extending from the handle. The sheath includes a lumen, a proximal end, a distal end, a proximal portion, an intermediate portion, and a distal portion. The intermediate portion of the sheath is more flexible than both the proximal portion and the distal portion of the sheath. The device also includes an object-engaging unit. The object-engaging unit and the sheath are moveable relative to each other to achieve a collapsed state of the object-engaging unit in which the object-engaging unit is collapsed within the lumen of the distal portion of the sheath, and another state in which the object-engaging unit extends from the distal end of the sheath.

In one embodiment of the device according to this aspect of the invention, the outside diameter of the intermediate sheath portion is more narrow than the outside diameter of the proximal and distal sheath portions. The intermediate sheath portion, in another embodiment, has one or more fewer layers than the proximal and distal sheath portions, and in this case the outside diameter of the intermediate sheath portion may or may not have the same outside diameter as the proximal and distal sheath portions.

Also in accordance with the invention, the intermediate sheath portion has at least two sections, and at least one of the sections has a different number of layers of material than at least one other of the sections. The sections can be arranged in a variety of different patterns such as circumferential, longitudinal, spiral, helical, and/or criss-cross patterns.

Also, in accordance with this aspect of the invention, the layers of the sheath in all portions of the sheath comprise various materials, such as fluorinated ethylenepropylene (FEP), polytetrafluoroethylene (PTFE), stainless steel braid, or polyimide. Regardless of the materials or the number of layers of material used to make the proximal, intermediate, and distal sheath portions, the diameter of the sheath lumen is the same or different in the proximal, intermediate, and distal sheath portions.

In another aspect, the invention relates to a sheath for a medical device, wherein the sheath comprises a wall extending from a proximal end of the sheath to a distal end of the sheath. The wall defines a lumen extending from the proximal sheath end to the distal sheath end. The wall includes a proximal portion, an intermediate portion, and a distal portion. The intermediate portion is more flexible than the proximal and distal portions. The lumen in the distal portion of the sheath wall is adapted for receiving an object-engaging unit.

In still other aspects of the invention, methods of manipulating material in a body include inserting into a body (either directly or through some other mechanism such as an endoscope channel) a medical device including a sheath of the type described above. The steps of the methods include moving the object-engaging unit from a collapsed state to another state in which the object-engaging unit is extended beyond the distal end of the sheath, engaging the material in the body, and ultimately withdrawing the device from the body.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 2A illustrates a plan view of an embodiment of a medical device including a sheath according to the invention with an object-engaging unit in a fully extended or open position.

FIG. 2B illustrates the device illustrated in FIG. 2A with the object-engaging unit in a collapsed or retracted position within the distal end of the sheath.

FIG. 3A illustrates a plan view of another embodiment of a medical device including a sheath according to the invention with an object-engaging unit in a fully-extended, open position.

FIG. 3B illustrates the device illustrated in FIG. 3A with the object-engaging unit in a collapsed or retracted position within the distal end of the sheath.

FIG. 4A illustrates a plan view of an embodiment of the sheath according to the invention.

FIG. 5A illustrates a cross-section of an embodiment of the distal portion of a sheath according to the invention.

FIG. 5B illustrates a cross-section of an embodiment of the intermediate portion of the sheath illustrated in FIG. 5A according to the invention.

FIG. 7A illustrates a plan view of an embodiment of the sheath according to the invention, the intermediate portion including sections having different numbers of layers of material.

FIG. 7B illustrates a cross-section of the sheath illustrated in FIG. 7A taken at line 7B-7B.

FIG. 7C illustrates a cross-section of the sheath illustrated in FIG. 7A taken at line 7C-7C.

FIG. 7D illustrates a plan view of another embodiment of the sheath according to the invention, the intermediate portion including sections having different numbers of layers of material.

FIG. 7E illustrates a plan view of another embodiment of the sheath according to the invention, the intermediate portion including sections having different numbers of layers of material.

FIG. 7F illustrates a plan view of another embodiment of the sheath according to the invention, the intermediate portion including sections having different numbers of layers of material.

FIG. 8A is a plan view of an embodiment of a sheath according to the invention including an attenuated sheath wall in the intermediate portion of the sheath.

FIG. 9A shows another embodiment of a sheath according to the invention including an attenuated wall in the intermediate portion of the sheath.

FIG. 9D shows another embodiment of a sheath according to the invention including an attenuated wall in the intermediate portion of the sheath.

FIG. 10A illustrates a plan view of the long axis of a sheath according to the invention, the intermediate portion of the sheath including numerous slits in the external wall of the sheath.

DESCRIPTION

Figure 1:
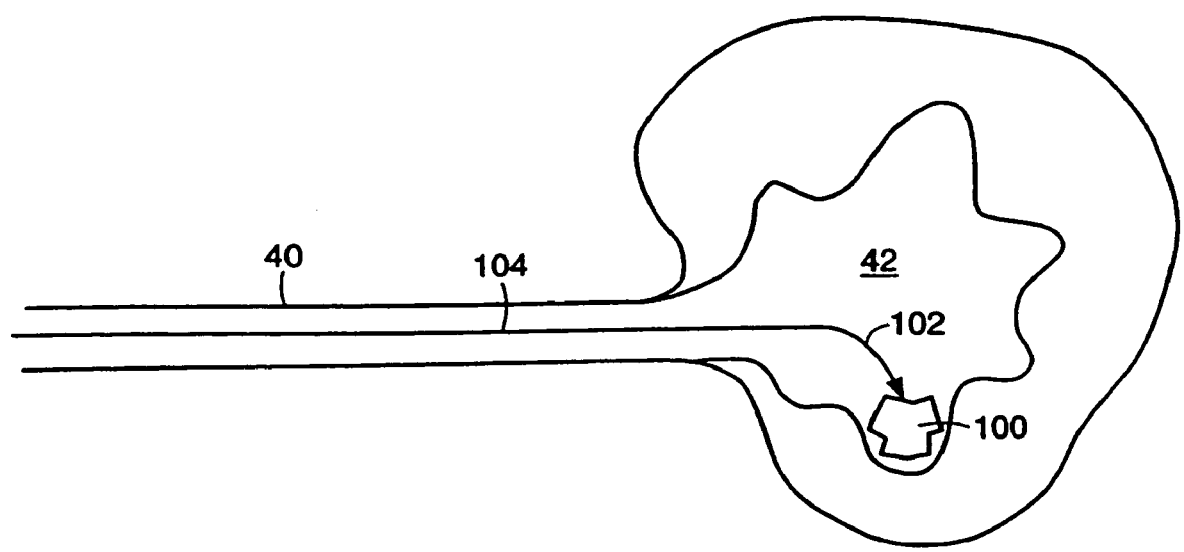
FIG. 1 illustrates a stone lodged in a remote body site.

One of the problems encountered when an elongated medical device, such as a retrieval device in a sheath, is used to reach a remote location in the body, is the turns and curves in the body tract that must be negotiated in order to reach the remote body location. As illustrated in FIG. 1, by way of example, a stone 100 lodged in the renal calyx 42 can not be approached via the ureter 40 without encountering at least one curve 102 illustrated by arrow 104. The rigid elongate member of a medical device can not effectively negotiate curves, such as the one illustrated, without causing tissue trauma in order to reach the remote tissue location.

According to the invention, positioning a flexible sheath portion near the distal end of the sheath, addresses this problem. The embodiments of the invention described below, all have the common feature of a flexible sheath portion positioned near the distal end of the elongated sheath.

All of the following embodiments of the invention have at least one thing in common, the sheath of the invention, on one hand, has sufficient flexibility in an area adjacent the distal end portion ( at the "intermediate portion" of the sheath) to allow engagement of a stone, tissue, or other material. On the other hand, the sheath has sufficient strength or rigidity at the most distal end portion of the sheath to enclose the object engaging unit in the inoperative or collapsed state and to permit the object-engaging unit to move in and out of the distal end portion of the sheath without the distal end portion of the sheath deforming or failing.

Referring to FIGS. 2A, 2B, 3A, and 3B, one embodiment of a medical device, according to the invention, includes a handle portion 16, an actuator 20, a sheath 14, a sheath lumen 15, an elongated member 18 that passes within the sheath lumen 15, and an object-engaging unit 10, such as the grasping forceps illustrated in FIGS. 2A and 2B. The handle 16, the sheath 14, and the object-engaging unit 10 are not shown in their correct size or proportion to each other. The sheath 14 typically is much longer and narrower than the handle 16 or the grasping forceps 10 to allow insertion into a body cavity or tract.

Referring to FIG. 4A, a sheath 14 according to the invention comprises at least three segments: a proximal segment 30, an intermediate segment 32, and a distal segment 34. The proximal segment 30 of the sheath is located nearest to the handle 16. The distal portion of the sheath 34 is that region of the sheath at the distal end of the medical device opposite to the handle 16. The intermediate portion 32 of the sheath is positioned distal to the proximal portion 30 of the sheath and proximal to the distal portion 34 of the sheath. The proximal end of the intermediate portion 32 of the sheath is located about 3 inches to 7 inches, preferably 4.75 inches, from the distal end 26 of the sheath.

The object-engaging unit 10 is collapsed within the distal portion of the sheath 34 for direct entry into the body or for entry into the body via the operating channel of an endoscope or laparoscope. The object-engaging unit 10 can be a grasping-type device, as illustrated in FIGS. 2A and 2B. Such grasping type object-engaging units are described in U.S. Ser. No. 09/064,704, the disclosure of which is expressly incorporated by reference herein. Other types of object-engaging units that can be used with the sheath of the invention are retrieval basket-type devices, as illustrated in FIGS. 3A and 3B, such as those described in U.S. Ser. No. 09/065,158, U.S. Ser. No. 09/027,534, U.S. Ser. No. 09/084,135, U.S. Ser. No. 09/296,327, U.S. Ser. No. 09/268,484, and U.S. Ser. No. 09/369,226, the disclosures of which are expressly incorporated by reference herein. Other suitable object-engaging units are forceps, probes, retractors, elevators, blades, needles, and the like.

Referring now to FIGS. 2A, 2B, 3A and 3B, the sheath 14, according to the invention, has at least one lumen 15 therein, and it extends from the handle 16 to a distal sheath end 26. In one embodiment, an elongated member 18, such as a cable, coil, shaft, guidewire, or mandril wire, extends within the lumen 15 from the actuating mechanism 20 in the handle portion 16 to a base 13 of the object engaging unit 10 where the elongated member 18 is joined to the object-engaging unit base 13. Operation of the actuating mechanism 20 by an operator causes the object-engaging unit 10 to move relative to the sheath 14 between a collapsed state within the distal sheath portion 34, as illustrated in FIG. 3B, to an extended state outside of the distal end 26 of the sheath 14 where the object-engaging unit 10 is open and extending beyond the distal end 26 of the sheath, as shown in FIG. 3A.

Alternatively, in another embodiment of the invention, the actuating mechanism is joined to the sheath. Operation of the actuating mechanism 20 by an operator in this embodiment causes the sheath 14 to move relative to the object-engaging unit 10 and the elongated member 18, such that the object-engaging unit 10 is moved between a collapsed position within the distal sheath portion 34, illustrated in FIG. 2B, to an extended position outside of the sheath 14 where the object-engaging unit 10 is open and extended beyond the distal end of the sheath 26 as illustrated in FIG. 2A.

With the object-engaging unit 10 withdrawn into and collapsed within the distal sheath portion 34, as shown in FIGS. 2B and 3B, the object-engaging unit 10 is inserted into the body directly, or via an endoscope channel, to a remote internal site in the body where the target material is located. The object-engaging unit 10 is then moved relative to the sheath 14 and placed in the extended position illustrated in FIGS. 2A and 3A, such that the object-engaging unit 10, in its operative position, is manipulated by the operator to engage the target material or tissue in the remote body site. The object-engaging unit 10 can then be used to manipulate the material in the body. Following manipulation of the material by the object-engaging unit 10, the object-engaging unit 10 is at least partially withdrawn into the lumen 15 of the distal sheath portion 34, as illustrated in FIG. 3B, by moving the elongated member 18 axially relative to the sheath 14 with the object-engaging unit 10 attached to its distal end, or by moving the sheath 14 axially relative to the object-engaging unit 10, as illustrated in FIG. 2B. The medical device, including the object-engaging unit 10 and the sheath 14, are withdrawn from the body cavity.

The overall length of the sheath 14, according to the invention, can range between 40 inches to 75 inches, preferably about 49.5 inches to 52.5 inches. The proximal portion 30 of the sheath is 35 inches to 55 inches in length, preferably 44.75 inches to 48.25 inches in length, the intermediate portion 32 of the sheath is 3 inches to 6 inches in length, preferably 3.5 to 4.0 inches, and the distal portion 34 of the sheath is 0.10 inches to 1.0 inch in length, preferably 0.75 inches.

The outside diameter 11 of the sheath, indicated between the arrows 11 in FIG. 4A, may or may not be uniform from the proximal end of the sheath 24 to the distal end of the sheath 26. In general, the outside diameter 11 of the proximal sheath portion 30 may range from 0.0315 inches to 0.0414 inches, the outside diameter 11 of the intermediate sheath portion 32 may range from 0.03 inches to 0.0445 inches, and the outside diameter 11 of the distal sheath portion 34 may range from 0.0315 inches to 0.0445 inches.

Figure 4B:
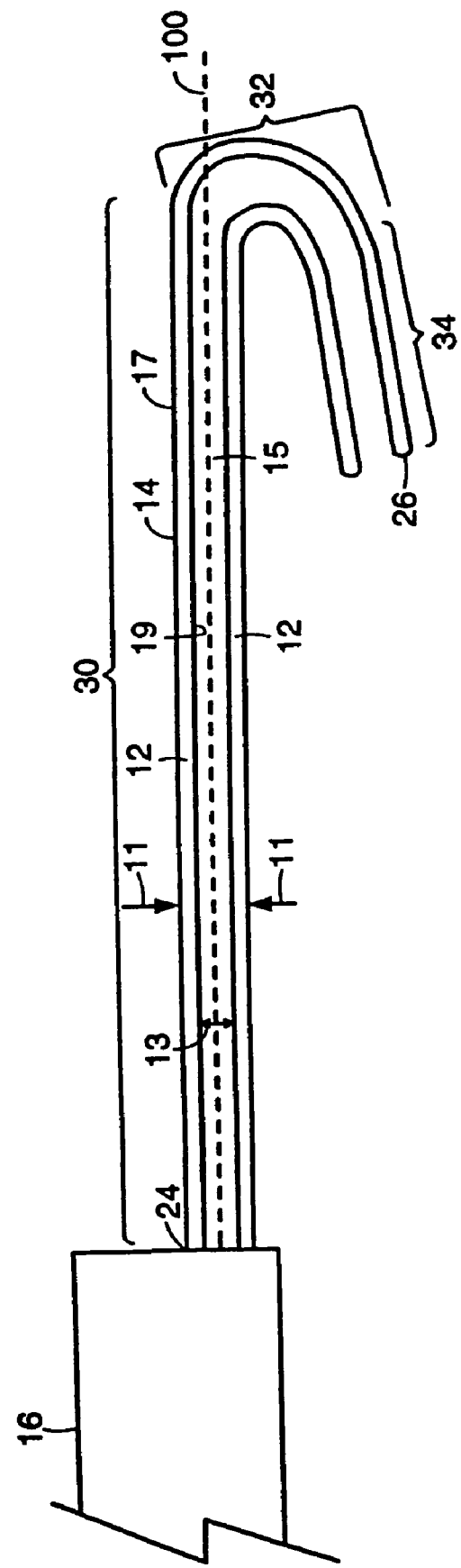
FIG. 4B illustrates a plan view of a sheath when the intermediate sheath portion is flexed.

Sheath flexibility varies along the sheath's long axis from the proximal end 24 of the sheath to the distal end 26 of the sheath. In one embodiment, according to the invention, the intermediate portion 32 of the sheath 14 is more flexible than either the proximal sheath portion 30 or the distal sheath portion 34. That is, the proximal sheath portion 30 and the distal sheath portion 34 are more rigid than the intermediate sheath portion 32. The flexibility of the proximal sheath portion 30 and the distal sheath portion 34 can be the same or can differ. However, the proximal sheath portion 30 and the distal sheath portion 34 are less flexible, i.e., more rigid, than the intermediate sheath portion 32. The intermediate portion 32 is highly flexible, as illustrated in FIG. 4B, and can be flexed to as much as 360 degrees from the long axis of the sheath (indicated as reference line 100). After the sheath of the invention is inserted into a channel of a flexible endoscope, the flexible endoscope with the sheath may flex as much as 180 degrees to 190 degrees.

Enhanced flexibility of the intermediate portion 32 of the sheath 14 is achieved in several ways. Referring to FIGS. 4A, 4B, 5A, 5B, 6A and 6B, in one embodiment of a sheath 14, according to the invention, the sheath 14 is constructed with layers of material extending from the luminal side 19 of the sheath wall 12 to the outside 17 of the sheath wall 12. The wall 12 of the sheath, according to the invention, includes multiple concentric layers of the same or different materials. The intermediate sheath portion 32, like the proximal sheath portion 30 and the distal sheath portion 34, includes multiple concentric layers, however, the intermediate sheath portion 32 has at least one fewer layer or at least one different layer of material than the layers of material in the proximal sheath portion 30 and the distal sheath portion 34.

For example, as illustrated by a cross-section of distal sheath 34 in FIG. 5A, in one embodiment of the sheath, according to the invention, the distal sheath portion 34 and the proximal sheath portion 30 (not shown) are manufactured from four layers of material including, from inside 19 of the sheath wall 12 to outside 17 of the sheath wall 12, a first layer (a) of polytetrafluoroethylene (PTFE), a second layer (b) of 304 braided stainless steel, a third layer (c) of polyimide, and a fourth layer (d) of fluorinated ethylenepropylene (FEP). Each material is arranged in a concentric layer around the circumference of the sheath wall 12. In the same sheath, the intermediate sheath portion 34, illustrated in FIG. 5B, has one fewer of the layers a-d than the proximal and distal sheath portions. The materials in intermediate sheath portion 32, from the inside 19 of the sheath wall 12 to the outside 17 of the sheath wall 12, include a first inner layer (a) of PTFE, a second layer (b) of stainless steel braid, no third layer, and a fourth layer (d) of FEP, each material arranged in a concentric layer around the circumference of the sheath wall 12. The relative thickness of each layer, illustrated in FIGS. 5A and 5B, is merely intended to be illustrative and is not limited to that illustrated. The thickness of one or more of the layers of the sheath wall 12 may be greater or lesser than the thickness of one or more of the other layers. Thus, the outer diameter 11 of the intermediate sheath portion 32 may be less than or the same as the outer diameter 11 of proximal sheath portion 30 and distal sheath portion 34. However, the internal diameter 13 of the intermediate sheath portion 32 is the same as the internal diameter 13 of proximal sheath portion 30 and distal sheath portion 34. That is, the diameter of the lumen 15 of the sheath 14 is uniform from the proximal end 24 of the sheath to the distal end 26 of the sheath. By maintaining a constant luminal internal diameter 13 throughout the length of the sheath 14, the object-engaging unit 10 and the elongated member 18 may move in the lumen 15 relative to the sheath 14 without becoming snagged.

In an alternate embodiment, the proximal sheath portion 30 and the distal sheath portion 34 are manufactured from a different combination of materials. For example, the first or inner layer is FEP, followed by a second layer of stainless steel braid, followed by a third layer of polyimide, and followed by a fourth, outer layer of PTFE. The intermediate sheath portion 32 of this embodiment of the sheath includes a first inner layer (a) of FEP, a second layer (b) of stainless steel braid, no third layer, and a fourth, outer layer (d) of PTFE.

Figure 6B:
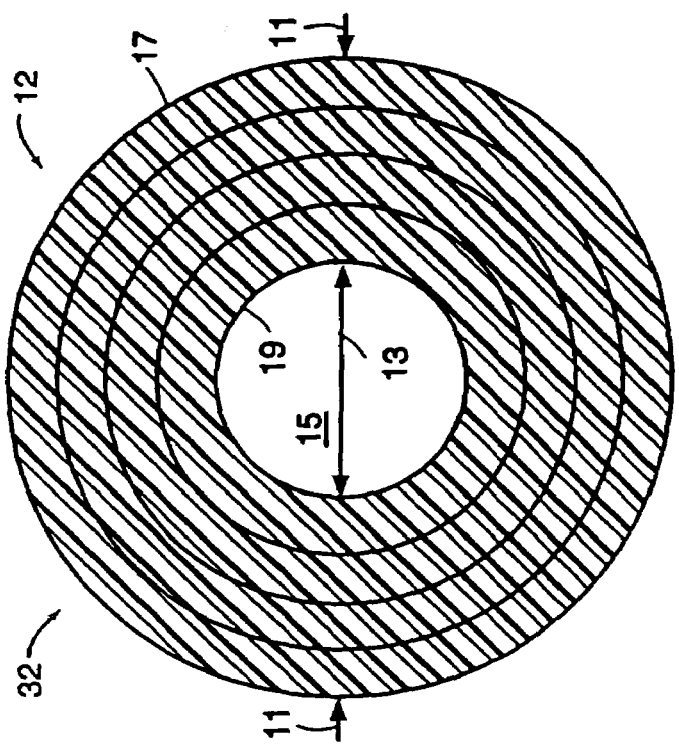
FIG. 6B illustrates a cross-section of an embodiment of the intermediate portion of the sheath illustrated in FIG. 6A according to the invention.
Figure 6A:
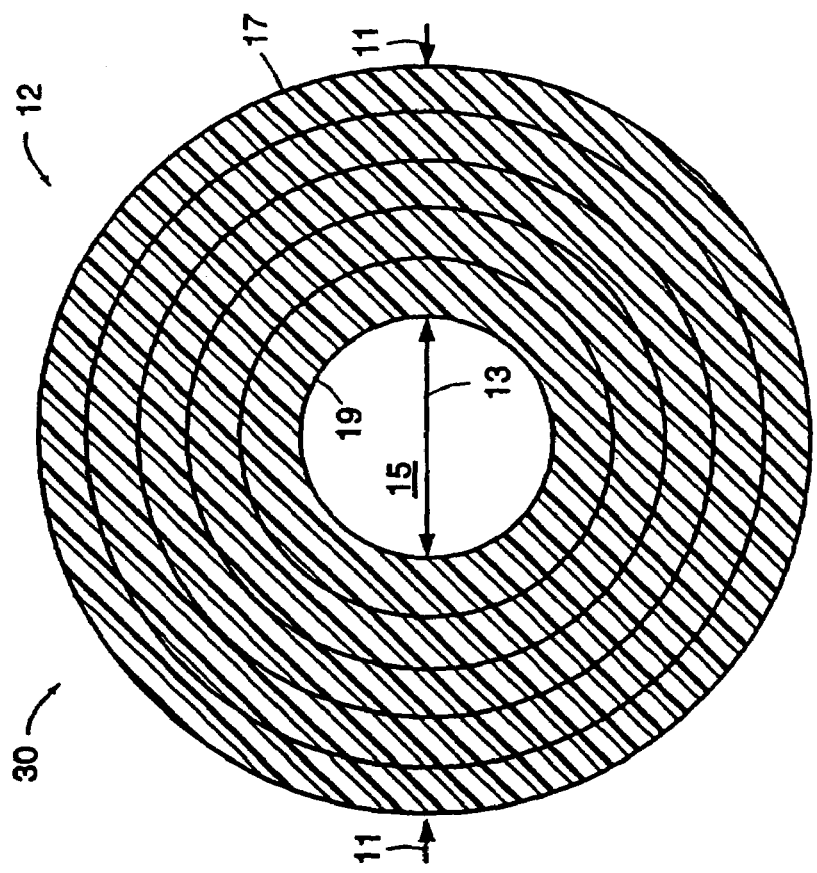
FIG. 6A illustrates a cross-section of another embodiment of a proximal portion of the sheath according to the invention.

In yet another embodiment of the sheath of the invention, the proximal sheath portion 30, illustrated in FIG. 6A, and the distal sheath portion 34 each have five layers, each layer made from the same material. In this embodiment of the sheath, the intermediate sheath portion 32, illustrated in FIG. 6B, has four layers of material identical to the material used in the five layers of the proximal 30 and distal 34 sheath portions. Other materials and different number of layers of the sheath are also contemplated by the invention and are not limited to those illustrated in FIGS. 5A, 5B, 6A and 6B. Whatever the combination of materials and numbers of layers, the intermediate sheath portion 32 is always more flexible than the proximal sheath portion 30 and distal sheath portion 34, and the internal diameter 13 of the sheath is uniform from the proximal end 24 of the sheath to the distal end 26 of the sheath.

In another embodiment of the sheath, the intermediate sheath portion 32 has at least two sections 33, 35, and at least one of the sections has a different number of layers of material than at least one other of the sections. A section of the sheath is a region of the sheath wall having a different number of layers than an adjacent region of the sheath wall. For example, as illustrated in FIG. 7A, the wall of the intermediate portion 32 of the sheath 17 can have a section of three layers 35 of material followed by a section of four layers 33 of material, followed by a section of three layers 35 of material, and so on. Alternatively, the wall of the intermediate portion 32 of the sheath can have a section of four layers of material, followed by a section of three layers of material, followed by a section of two layers of material, followed by a section of four layers of material, and so on. This pattern may be repeated along the entire length of the intermediate sheath portion 32 or the pattern may be limited to a portion of the intermediate sheath portion 32. The number and type of sections can be varied and different than the specific arrangements shown. The sections in the intermediate sheath portion 32 can be arranged circumferentially, spirally in a lattice-like or criss-cross pattern, or longitudinally, as illustrated in FIGS. 7A, 7D, 7E and 7F, respectively.

In one particular embodiment, the wall of the intermediate sheath portion 32 has a repeating pattern of four layer and three layer sections along its entire length, although other embodiments can have other layers in the sections. In a particular embodiment of the wall of the intermediate portion of the sheath having four layers, one of the four layers is polyimide while the other layers are selected from materials, such as FEP, stainless steel braid, PTFE, polyetheretherketone (PEEK), or Nitinol. In this embodiment, the polyimide layer is absent in the sections of the wall of the sheath having three layers. In other embodiments, a layer of a different material is absent in the wall of the intermediate sheath portion.

A sheath, according to the invention, has the advantage of enhanced flexibility while maintaining sheath column and compression strength. For example, in one embodiment of the sheath of the invention, the proximal sheath portion 30 and the distal sheath portion 34 have four layers in the sheath wall while the intermediate sheath portion 32, has a repeating pattern of a three layer section 35 followed by a four layer section 33. Alternatively, sections 33 have two, four, or more layers and sections 35 have a different number of layers than sections 33.

In one embodiment of the invention, the arrangement of sections in the intermediate sheath portion 32 may be circumferential as illustrated in FIGS. 7A, 7B and 7C. In this embodiment, each section 33, 35 is a band that wraps 360° around the circumference of the sheath wall. At least one of the sections 35 has fewer layers of material than an adjacent section 33.

In another embodiment, as illustrated in FIG. 7D, adjacent sections 33, 35 in the intermediate sheath portion 32 are spirally arranged. Rather than the sections being circumferentially arranged as illustrated in FIG. 7A, the sections in this embodiment spiral along all or a portion of the length of the wall of the intermediate sheath portion.

In yet another embodiment of the invention, as illustrated in FIG. 7E, the sections in the intermediate sheath portion 32 are arranged as two intersecting spirals along all or a portion of the intermediate sheath portion 32. In this embodiment of the intermediate sheath portion 32, looking at the side of the sheath 17, spiral sections 33, 33' appear as a plurality of "Xs" along all or a portion of the intermediate sheath portion. Sections 35 have a different number of layers of material than sections 33.

In still another embodiment of the invention, as illustrated in FIG. 7F, adjacent sections 33,35 in the intermediate sheath portion 32 are arranged longitudinally, paralleling the long axis of the sheath. In this embodiment of the intermediate sheath portion 32, one or more longitudinal sections 33, 35 are distributed around the circumference of the sheath along all or a portion of the intermediate sheath portion 32.

The embodiments illustrated in FIGS. 7A-7F are meant to be illustrative. Other arrangements of sections in the intermediate sheath portion are possible.

In another embodiment of the sheath, according to the invention, a first polymer having a certain characteristic stiffness is used to manufacture the sheath wall in the intermediate sheath portion 32 and a second polymer having a different characteristic stiffness than the first polymer can be used in the proximal sheath portion 30 and the distal sheath portion 34 (not shown). For example, a polymer-metal composition may be used in the intermediate sheath portion 32 whereas a more rigid or stiff type of polymer can be used in the proximal sheath portion 30 and the distal sheath portion 34. In general, any type of material may be used in the intermediate sheath portion 32 that is a suitable material having the appropriate strength, flexibility and biocompatibility characteristics.

Other materials that can be included in one or more layers of the sheath are polyetheretherketone (PEEK), or nickel-titanium (Nitinol) braid.

Figure 8D:
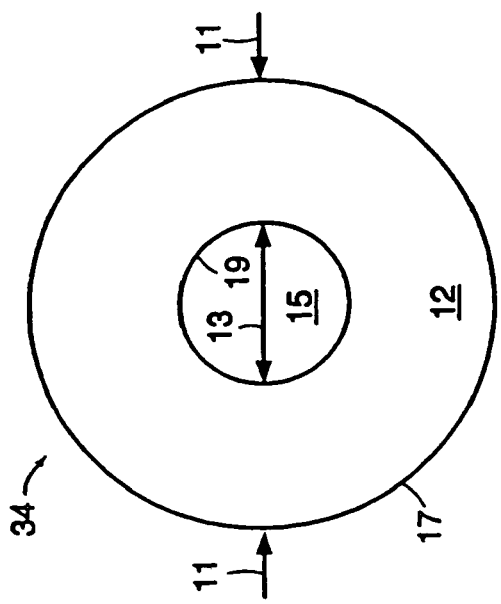
FIG. 8D illustrates a cross-section of the embodiment of the distal sheath portion illustrated in FIG. 8A taken at line 8d-8d.
Figure 8C:
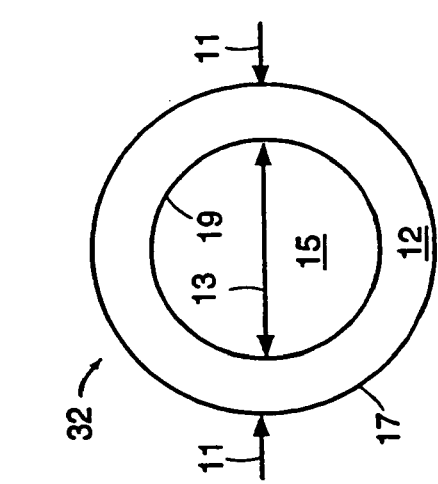
FIG. 8C illustrates a cross-section of the embodiment of the intermediate sheath portion illustrated in FIG. 8A taken at line 8c-8c.
Figure 8B:
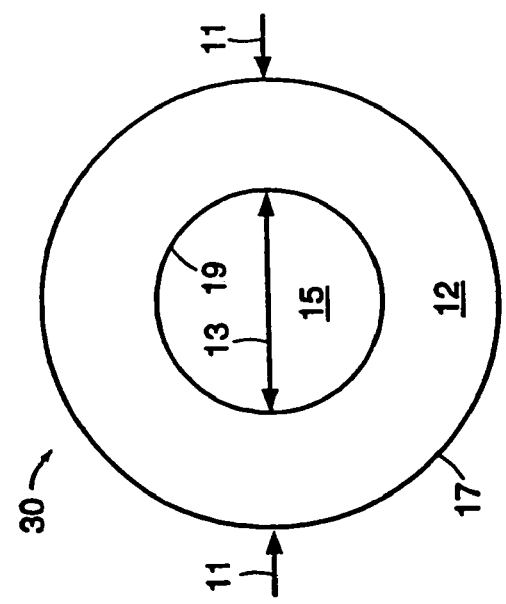
FIG. 8B illustrates a cross-section of the embodiment of the proximal sheath portion illustrated in FIG. 8A taken at line 8b-8b.

Referring now to FIG. 8A, in another embodiment, according to the invention, the outer diameter 11 of the sheath wall in the intermediate portion 32, is less than the thickness of the sheath wall at the proximal portion 30 and the thickness of the sheath wall at the distal sheath portion 34. As illustrated by cross-sections of proximal sheath portion 30 in FIG. 8B, and distal sheath portion 34 in FIG. 8D, the thickness of sheath wall 12 is the same in the proximal sheath portion 30 and distal sheath portion 34. As illustrated by cross-section of intermediate sheath portion 32 in FIG. 8C, the thickness of the intermediate sheath portion 32 is less than either the proximal sheath portion 30 illustrated in FIG. 8B and the distal sheath portion 34 illustrated in FIG. 8D. The inside diameter 13 of the sheath in the intermediate portion 32 of the sheath, illustrated in FIG. 8C, is unchanged relative to the inside diameter 13 of proximal sheath portion 30, illustrated in FIG. 8B, and distal sheath portion 34, illustrated in FIG. 8D. By maintaining a uniform inside diameter 13 from the proximal end 24 of the sheath to the distal end 26 of the sheath, illustrated in FIG. 8A, an object-engaging unit can slide smoothly in the lumen 15 of the sheath without risk of snagging in dilated or constricted regions of the inner wall 13 of the sheath.

Figure 9B:
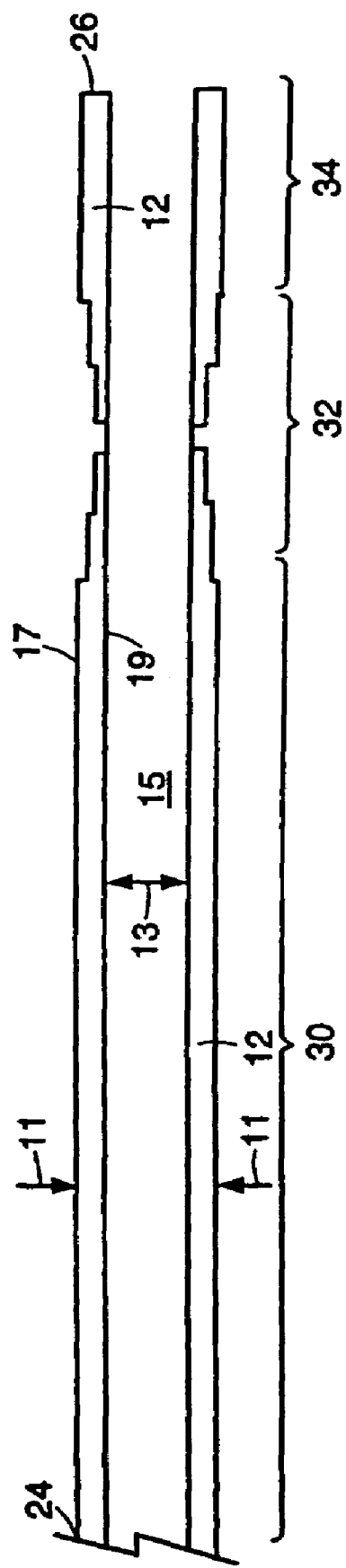
FIG. 9B shows another embodiment of a sheath according to the invention including an attenuated wall in the intermediate portion of the sheath.
Figure 9C:
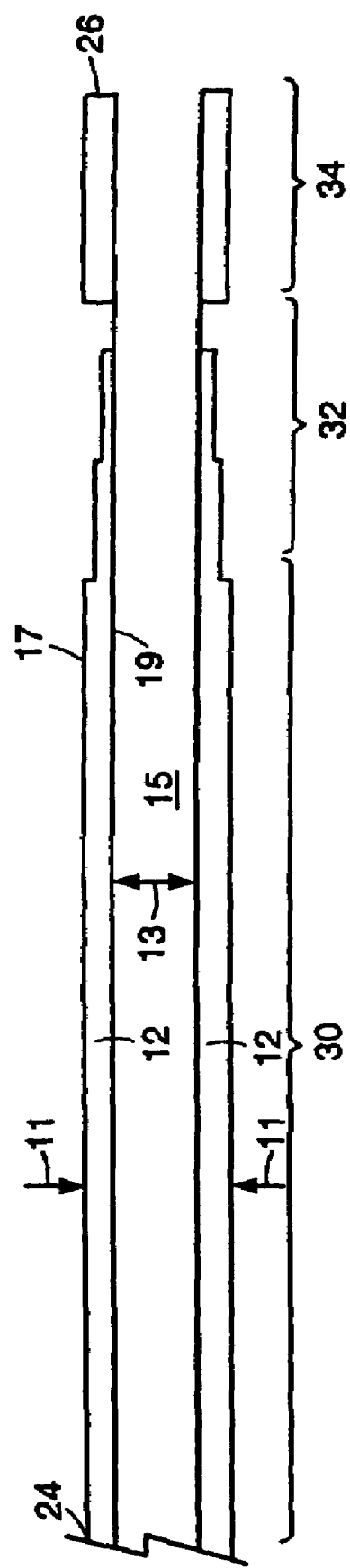
FIG. 9C shows another embodiment of a sheath according to the invention including an attenuated wall in the intermediate portion of the sheath.

In one embodiment, illustrated in FIG. 8A, the transition in wall 12 thickness along the intermediate portion 32 of the sheath is gradual. In an alternate embodiment, the transition in wall thickness of the intermediate sheath portion 32, relative to the wall thickness of proximal sheath portion 30 and distal sheath portion 34, is incremental, i.e., occurs in multiple stages, segments, or steps as illustrated in FIG. 9A. The number of possible incremental steps is without limit. The increments in wall thickness can be non-uniformly distributed along the long axis of intermediate sheath portion 32 as illustrated in FIGS. 9B and 9C. The inside diameter 13 of the sheath wall 12 is uniform from the proximal sheath portion 30, the intermediate sheath portion 32, to the distal sheath portion 34. As a result, the diameter of the sheath lumen 15 is unchanged throughout the length of the sheath from the proximal end 24 to the distal end 26 of the sheath 14.

Referring to FIG. 9D, in another embodiment of the sheath of the invention, the external sheath wall 17 of the intermediate sheath portion 32 is thrown into circumferential folds to achieve an accordion-like effect. This accordion-like effect enhances the flexibility of the intermediate sheath portion 32 relative to the rest of the sheath 14. The inner diameter of the sheath in the intermediate sheath portion 32 is unchanged relative to the inner diameter of proximal sheath portion 30 and distal sheath portion 34. The diameter of the lumen 15 of the sheath, therefore, is constant from the proximal end 24 of the sheath to the distal end 26 of the sheath.

Figure 10B:
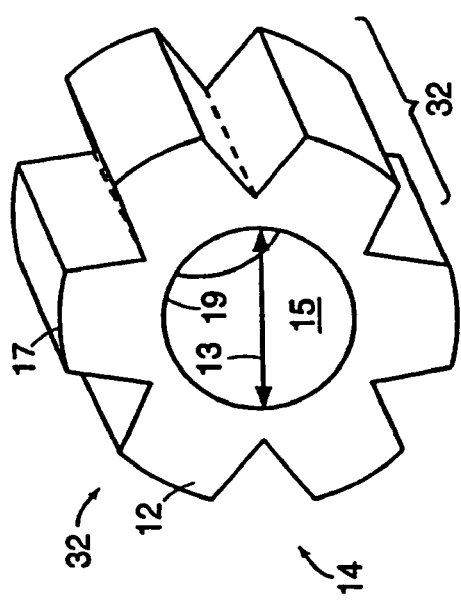
FIG. 10B shows a cross-section in perspective of the embodiment of the intermediate portion of the sheath illustrated in FIG. 9A at 9b-9b.
Figure 10C:
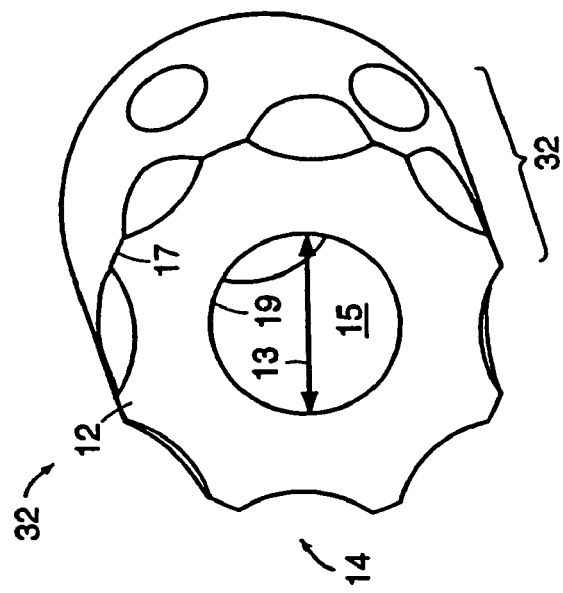
FIG. 10C shows a cross-section in perspective of another embodiment of the intermediate portion of a sheath according to the invention including numerous depressions in the external wall of the sheath.

Referring to FIGS. 10A-10C, in another embodiment of the invention, flexibility may be added to the intermediate portion 32 of the sheath by modification of the external sheath wall 17 with slits, grooves, or other depressions. Slits, grooves, or depressions can be distributed completely or partially around the circumference of the sheath wall 12 in the intermediate sheath portion 32 as illustrated in FIG. 10A. As illustrated by a cross-section in perspective of intermediate sheath portion 32 in FIG. 10B, the modifications in the external sheath wall 17 of the intermediate sheath portion 32 extend part way through the full thickness of the sheath wall 12 and not through the inner sheath wall 19. Sheath wall modifications, such as slits or grooves, are oriented with their long axis anywhere from parallel to perpendicular to the long axis of the sheath.

As illustrated in FIG. 10C, in yet another embodiment of the sheath of the invention, scattered dimples or other shapes are introduced into the outer sheath wall 17 of the intermediate sheath portion 32. Like the grooves or slits illustrated in FIG. 10B, dimples extend from the outer wall 17 partially into the sheath wall 12 but not through the inner sheath wall 19. Thus, as illustrated in FIGS. 10B and 10C, the inner diameter 13 of the sheath and, therefore, the sheath lumen 15, is uniform throughout the length of the sheath beginning at the proximal end 24 of the sheath, extending through the intermediate portion 32 of the sheath, to the distal end 26 of sheath 14.

The surface of the sheath 14, from the proximal portion 24 to the distal portion 26, is made or coated with any suitable material with a low friction coefficient, such as a polymeric material, a polyethylene glycol, a photopolyacrylamide-heparin complex, hyaluronic acid, polyvinylpyrrolidine material, and others. These low-friction materials are materials included in the composition of the sheath wall during manufacturing or applied to the surface of the sheath after the sheath is manufactured.

The sheath of the invention provides numerous advantages. For example, the flexible intermediate portion 32 of the sheath allows an increase in the deflection capability of the sheath 14. When inserted into a flexible scope, for example, the flexible intermediate portion 32 of the sheath 14 overcomes the rigidity of the distal end 26 of the sheath that is necessary for the proper actuation of the object-engaging unit 10. The flexible intermediate portion 32 coincides and deflects with a bending portion of the flexible scope without substantially impairing the capacity of the endoscope to flex.

The distal portion 34 of the sheath holds and surrounds the object-engaging unit 10 when it is in the collapsed state or partially collapsed state, without radial deformation of the sheath 14. The flexible intermediate portion 32 of the sheath allows more steerability than possible with conventional sheaths.

In another aspect, the invention relates to a method for manipulating material or tissue in a body, such as a body tract or body canal, with a medical device including a sheath. The sheath, as part of the medical device, may be introduced directly into the body cavity or may be introduced through a channel in an endoscope or laparoscope. Sheaths, according to the invention, provide the requisite rigidity at the proximal sheath portion 30 for effective manipulation by an operator for locating, engaging, and retrieving stones, and the requisite rigidity at the distal sheath portion 34 to enclose the object-engaging unit 10 in the collapsed or partially collapsed state without deformation or distortion of the distal end of the sheath. Sheaths of the invention can be introduced into an endoscope or laparoscope without the need for introducers or other means. When the sheath is inserted into a flexible endoscope, the flexible intermediate portion 32 of the sheath allows the endoscope to flex to reach a remote body site. With the sheath inserted into a channel of the endoscope, the endoscope can flex about 180 to 190 degrees. Sheaths of variable strengths, according to the invention, are used with medical retrieval devices or a variety of other medical devices. Also, the sheaths of the invention can be used in urology, endoscopy, laparoscopy, biliary, and lithotripsy procedures as well as a variety of other applications.

Figure 11A:
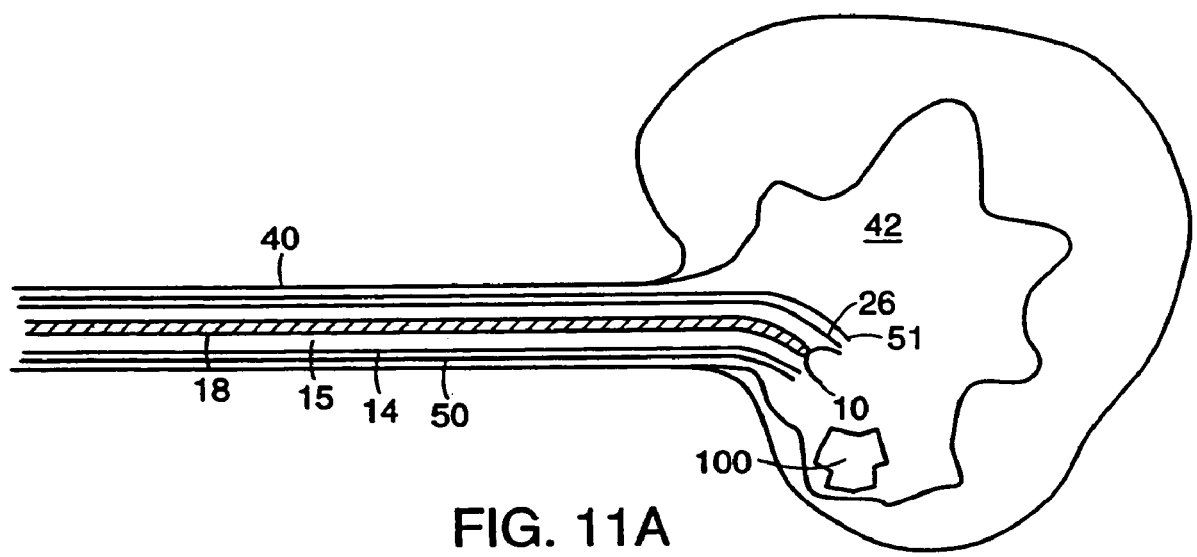
FIG. 11A illustrates a first step in a method for retrieving material located in a body cavity using a medical device including a sheath according to the invention.
Figure 11B:
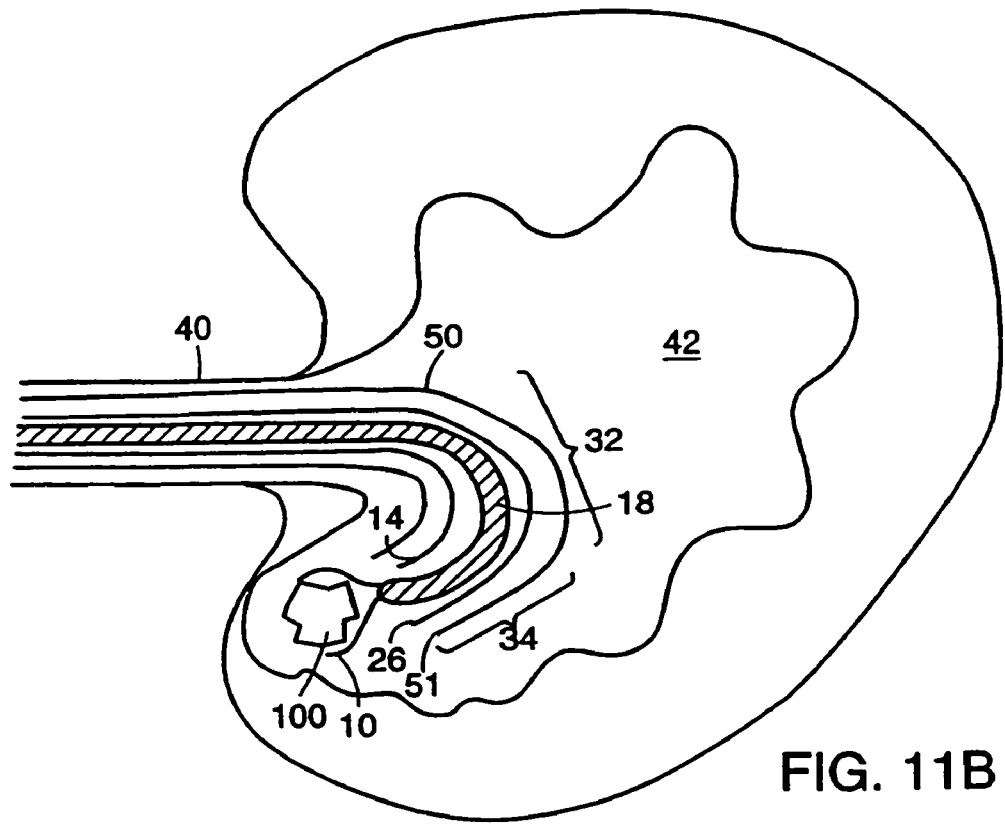
FIG. 11B illustrates a second step in a method for retrieving material from a body cavity using a medical device including a sheath according to the invention.
Figure 11C:
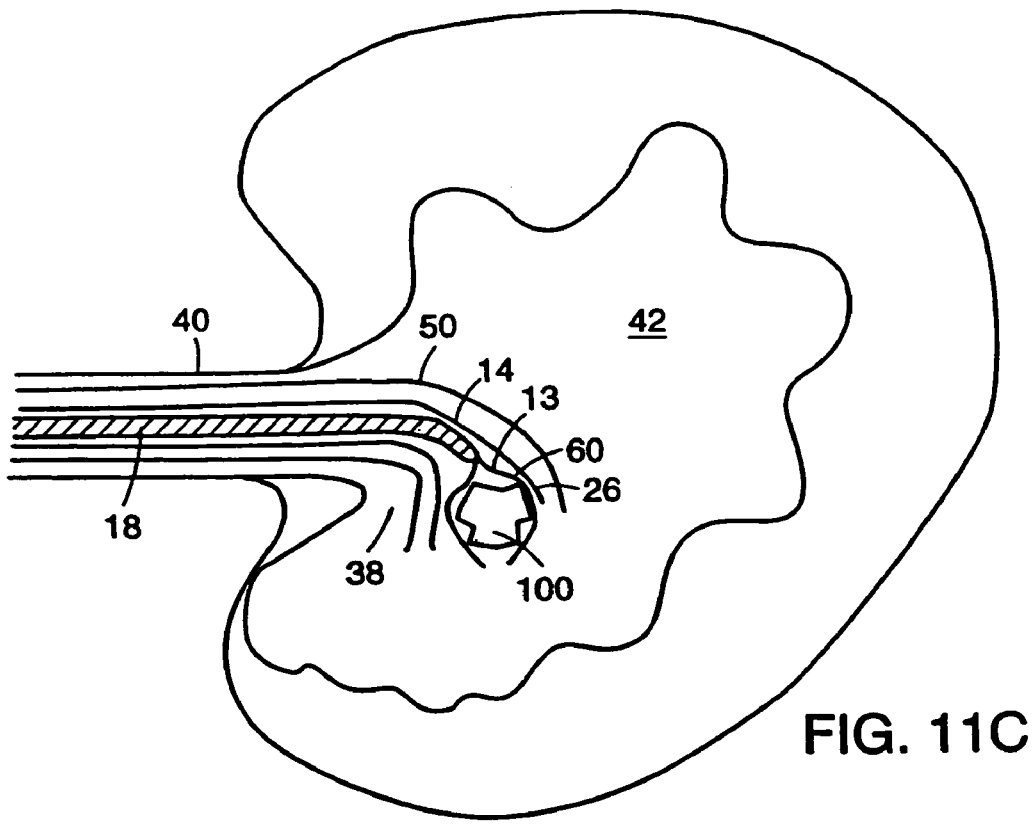
FIG. 11C shows a third step in a method for retrieving material from a body cavity using a medical device including a sheath according to the invention.

Referring to FIGS. 11A-11C, a method for retrieving material from a patient includes inserting a medical device including a sheath according to the invention into the patient. The medical device including the sheath according to the invention may be directly introduced into the patient or may be introduced via a channel 50 of an endoscope or laparoscope as illustrated in FIG. 11A. For example, the endoscope 50 is advanced by an operator via the lumen of the ureter 40 until the distal end of the endoscope 50 enters the patient's body site, such as the renal pelvis 42, where the target material 100 is located. The medical device, including the object-engaging unit 10 collapsed within the distal end portion 34 of the sheath, is passed into the endoscope 50, until the distal end 26 of the sheath approaches the distal end 51 of the endoscope 50. As shown in FIG. 11B, the flexible intermediate portion 32 of the sheath coincides and deflects with the bending portion of the flexible endoscope 50. The object-engaging unit 10 is extended from the distal end 26 of the sheath 14 to manipulate the material or tissue 100 within the remote body site 42. The distal end portion 34 of the sheath is of sufficient strength and rigidity to resist deformation of the sheath as the object-engaging unit 10 is moved relative to the sheath.

As shown in FIG. 11C, after the material or tissue 100 within the remote body site 42 is manipulated, the object-engaging unit 10 is withdrawn partially or completely into the distal end portion 34 of the sheath either by axial movement of the elongated member 18, attached to the base 13 of the object-engaging unit 10, or by movement of the sheath 14 over the stationary object-engaging unit 10.

The medical device including the sheath according to the invention can be directly inserted (not shown) into a body cavity without an endoscope or an introducer. The steps are similar to those described above for use of the medical device in an endoscope. The flexible intermediate portion of the sheath 32 deflects against the wall of the body tract as the sheath housing the object-engaging unit is advanced in the body tract. The object-engaging unit extends from the distal end of the sheath in the manner described above for using the medical device in an endoscope. After the material in the body site is manipulated, the object-engaging unit is withdrawn partially or completely into the distal sheath portion. The medical device including the sheath is withdrawn from the body tract.

Variations, modifications, and other instrumentations of what is described herein will occur to those of ordinary skill in the art without departing from the spirit and scope of the invention as claimed. Accordingly, the invention is to be defined not by the preceding illustrative description but instead by the spirit and scope of the following claims.

What is claimed is:

1. A device for manipulation of material in a body, comprising:
   a handle;
   a sheath extending from the handle and comprising at least one lumen, a distal end, a proximal portion, a distal portion, and an intermediate portion, each of the proximal, intermediate, and distal portions being comprised of multiple layers of material and configured for insertion in a body cavity, the intermediate portion of the sheath being more flexible than the proximal and distal portions of the sheath and comprising at least one fewer layer of material than the layers of material in the proximal and distal portions; and
   an object engaging unit, the object-engaging unit and sheath moveable relative to each other to achieve a collapsed state of the object-engaging unit in which the object-engaging unit is collapsed within the lumen of the distal portion of the sheath and another state in which the object-engaging unit extends from the distal end of the sheath, wherein the distal portion of the sheath comprises sufficient rigidity to resist deformation of the distal portion of the sheath when the object-engaging unit moves relative to the sheath.

2. The device of claim 1, wherein the proximal portion is substantially longer than the intermediate portion.

3. The device of claim 1, wherein each of the proximal, intermediate, and distal portions are comprised of multiple layers of material.

4. The device of claim 1, wherein said object-engaging unit is selected from the group consisting of forceps and a retrieval basket.

5. The device of claim 1, wherein the outside diameter of said intermediate portion is narrower than the outside diameter of said proximal and said distal portions.

6. The device of claim 1, wherein the intermediate portion includes a proximal end and a distal end, the proximal portion extending from a proximal end of the sheath to the proximal end of the intermediate portion, and the distal portion extending from the distal end of the intermediate portion to a distal-most end of the sheath.

7. The device of claim 1, wherein the intermediate portion includes at least one fewer layer of material around the entire outer circumference of the intermediate portion than the proximal and distal portions of the sheath.

8. The device of claim 1, wherein, in a cross-section of the distal portion, an outermost layer of material of the distal portion maintains a substantially uniform thickness around an outer circumference of the distal portion.

9. The device of claim 1, wherein, in a cross-section of the proximal portion, an outermost layer of material of the proximal portion maintains a substantially uniform thickness around an outer circumference of the proximal portion.

10. A method of manipulating a material in a body tract, comprising:

inserting into an endoscope a medical device comprising a handle, a sheath extending from the handle, the sheath comprising at least one lumen, a distal end, a proximal portion, a distal portion, and an intermediate portion, each of the proximal, intermediate, and distal portions being comprised of multiple layers of material and configured for insertion in a body cavity, the intermediate portion of the sheath being more flexible than the proximal and distal portions of the sheath and comprising at least one fewer layer of material than the layers of material in the proximal and distal portions, and an object-engaging unit, the object-engaging unit and sheath movable relative to each other to achieve a collapsed position of the object-engaging unit in which the object-engaging unit is within the lumen of the distal portion of the sheath, and an extended position in which the object-engaging unit extends from the distal end of the sheath, and the distal portion of the sheath comprising sufficient rigidity to resist deformation of the distal portion of the sheath when the object-engaging unit moves relative to the sheath;

moving the object-engaging unit relative to the sheath from the collapsed state within the distal end of the sheath, to another state in which the object-engaging unit is extended beyond the distal end of the sheath;

engaging the material to be manipulated in the body tract; and withdrawing the medical device from the body tract.

11. The method of claim 10, wherein the proximal portion is substantially longer than the intermediate portion.

12. The method of claim 10, wherein each of the proximal, intermediate, and distal portions are comprised of multiple layers of material.

13. The method of claim 10, wherein said object-engaging unit is selected from the group consisting of forceps and a retrieval basket.

14. The method of claim 10, wherein the outside diameter of said intermediate portion is narrower than the outside diameter of said proximal and said distal portions.

15. The method of claim 10, wherein the intermediate portion includes a proximal end and a distal end, the proximal portion extending from a proximal end of the sheath to the proximal end of the intermediate portion, and the distal portion extending from the distal end of the intermediate portion to a distalmost end of the sheath.

16. The method of claim 10, wherein the intermediate portion includes at least one fewer layer of material around the entire outer circumference of the intermediate portion than the proximal and distal portions of the sheath.

17. The method of claim 10, wherein, in a cross-section of the distal portion, an outermost layer of material of the distal portion maintains a substantially uniform thickness around an outer circumference of the distal portion.

18. The method of claim 10, wherein, in a cross-section of the proximal portion, an outermost layer of material of the proximal portion maintains a substantially uniform thickness around an outer circumference of the proximal portion.

* * * * *